(12) United States Patent
Picone

(10) Patent No.: US 11,547,289 B1
(45) Date of Patent: Jan. 10, 2023

(54) ENDOSCOPIC CLEANING AND LUBRICATION SYSTEM

(71) Applicant: Eric Picone, Huntersville, NC (US)

(72) Inventor: Eric Picone, Huntersville, NC (US)

( * ) Notice: Subject to any disclaimer, the term of this patent is extended or adjusted under 35 U.S.C. 154(b) by 417 days.

(21) Appl. No.: 16/716,690

(22) Filed: Dec. 17, 2019

(51) Int. Cl.
| | |
|---|---|
| *A61B 1/12* | (2006.01) |
| *B05C 13/02* | (2006.01) |
| *B05C 1/06* | (2006.01) |
| *B05C 11/10* | (2006.01) |
| *B08B 9/032* | (2006.01) |
| *A61B 1/00* | (2006.01) |
| *A61B 90/70* | (2016.01) |

(52) U.S. Cl.
CPC .......... *A61B 1/122* (2013.01); *A61B 1/00147* (2013.01); *A61B 1/121* (2013.01); *B05C 1/06* (2013.01); *B05C 11/10* (2013.01); *B05C 13/02* (2013.01); *B08B 9/032* (2013.01); *A61B 2090/701* (2016.02)

(58) Field of Classification Search
CPC ..... A61B 1/122; A61B 1/00147; A61B 1/121; A61B 2090/701; B05C 1/06; B05C 11/10; B05C 13/02; B08B 9/032
See application file for complete search history.

(56) References Cited

U.S. PATENT DOCUMENTS

| | | | |
|---|---|---|---|
| 4,517,702 A | 5/1985 | Jackson | |
| 5,711,921 A * | 1/1998 | Langford | A61B 90/70 422/294 |
| 5,753,195 A * | 5/1998 | Langford | A61B 90/70 422/294 |
| 8,196,248 B2 | 6/2012 | Kritzler | |
| 9,408,931 B1 * | 8/2016 | Ricciardi | A61L 2/16 |
| D765,840 S | 9/2016 | Miller | |
| 2003/0190256 A1* | 10/2003 | Halstead | A61B 1/123 422/1 |
| 2007/0169799 A1* | 7/2007 | Noguchi | G01M 3/26 15/301 |
| 2007/0234494 A1 | 10/2007 | Suziki | |
| 2009/0044845 A1* | 2/2009 | Cui | A61B 1/123 134/201 |
| 2009/0205687 A1* | 8/2009 | Onishi | F16L 37/127 134/136 |
| 2011/0152609 A1* | 6/2011 | Trusty | A61B 1/00149 600/102 |

(Continued)

*Primary Examiner* — Benjamin L Osterhout
(74) *Attorney, Agent, or Firm* — Kyle A. Fletcher, Esq.

(57) ABSTRACT

The endoscopic cleaning and lubrication system is a mechanical structure. The endoscopic cleaning and lubrication system is a medical device. The endoscopic cleaning and lubrication system clamps an endoscope to a working surface, such as an operating table, such that the endoscope can be cleaned and lubricated before use. The endoscopic cleaning and lubrication system comprises an endoscope clamp, a clamp mount, a gooseneck tube, and a table clamp. The gooseneck tube attaches the clamp mount to the table clamp. The table clamp attaches the endoscopic cleaning and lubrication system to the working surface. The clamp mount attaches the endoscope clamp to the gooseneck tube. The endoscope attaches to the endoscope clamp. The endoscope clamp holds the endoscope in a fixed position relative to the endoscopic cleaning and lubrication system. The gooseneck tube is a flexible structure that allows for the repositioning of the endoscope clamp.

19 Claims, 6 Drawing Sheets

(56) References Cited

U.S. PATENT DOCUMENTS

| | | | |
|---|---|---|---|
| 2011/0152878 A1* | 6/2011 | Trusty | A61B 1/00154 |
| | | | 606/130 |
| 2016/0331221 A1 | 11/2016 | Patzek | |
| 2017/0172397 A1* | 6/2017 | Zardini | A61B 1/125 |
| 2018/0078115 A1* | 3/2018 | Gupta | A61B 1/00066 |
| 2018/0147022 A1 | 5/2018 | Gupta | |
| 2018/0166495 A1 | 6/2018 | Nanyang | |
| 2019/0388573 A1* | 12/2019 | Nguyen | A61L 2/18 |

* cited by examiner

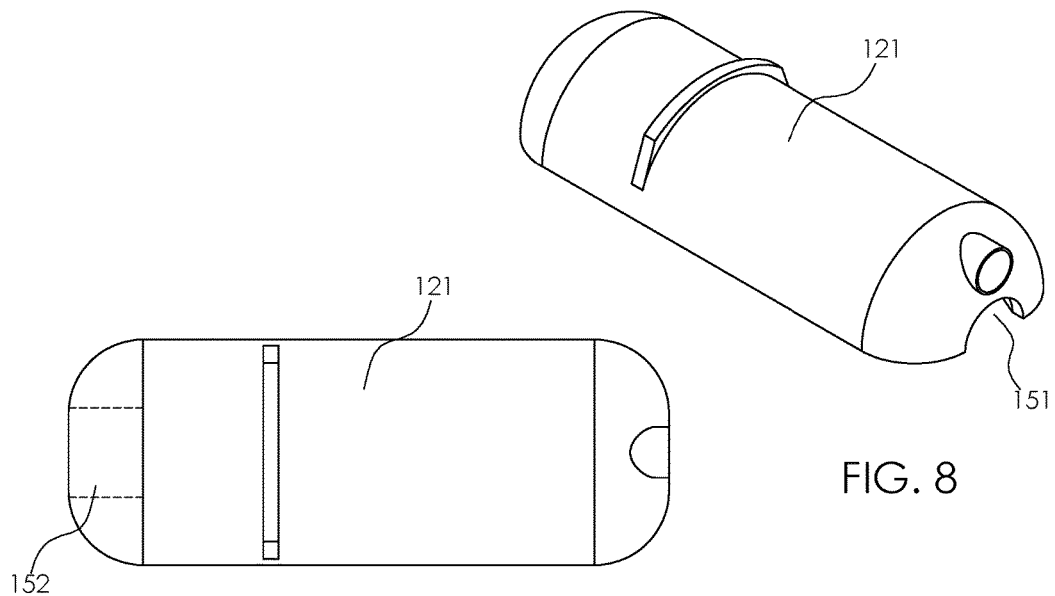
FIG. 8
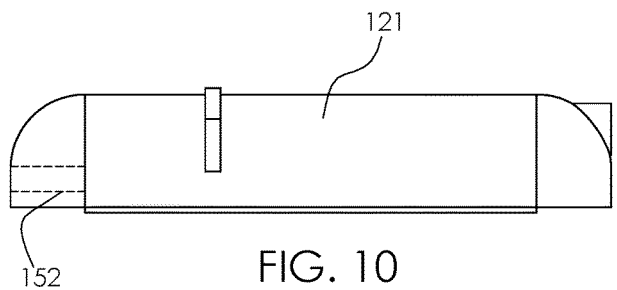
FIG. 9
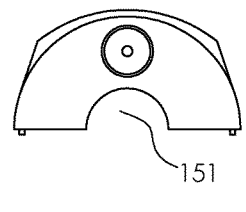
FIG. 10
FIG. 11
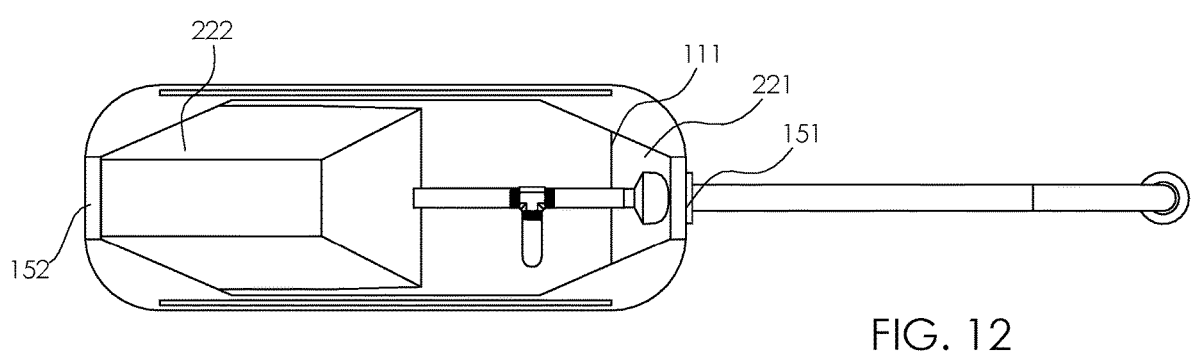
FIG. 12

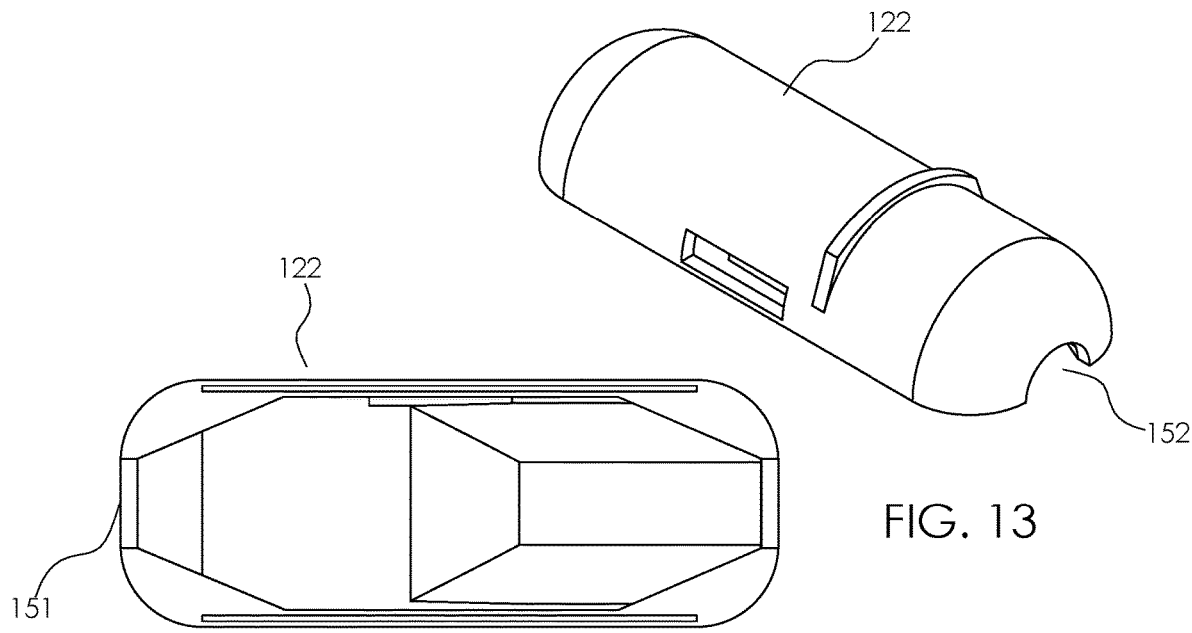
FIG. 13
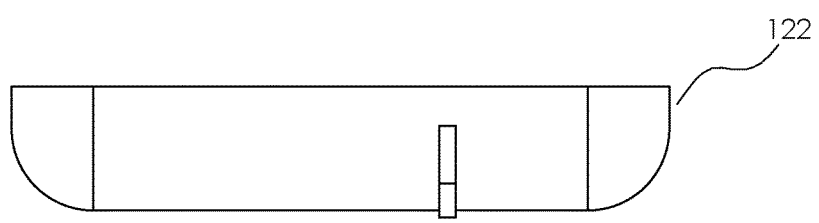
FIG. 14
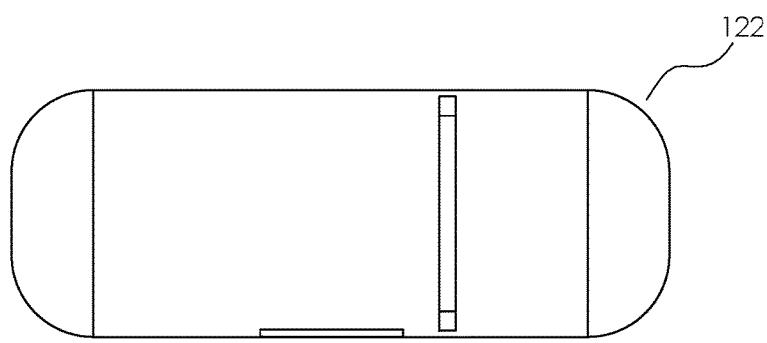
FIG. 15
FIG. 16 ically,
ENDOSCOPIC CLEANING AND LUBRICATION SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including instruments for examining the interior cavities of a body, more specifically, an accessory for an endoscope. (A61B1/00131)

SUMMARY OF INVENTION

The endoscopic cleaning and lubrication system is a mechanical structure. The endoscopic cleaning and lubrication system is a medical device. The endoscopic cleaning and lubrication system clamps an endoscope to a working surface, such as an operating table, such that the endoscope can be cleaned and/or lubricated before/during/after use in a medical procedure. The endoscopic cleaning and lubrication system comprises an endoscope clamp, a clamp mount, a gooseneck tube, and a table clamp. The gooseneck tube attaches the clamp mount to the table clamp. The table clamp attaches the endoscopic cleaning and lubrication system to the working surface. The clamp mount attaches the endoscope clamp to the gooseneck tube. The endoscope attaches to the endoscope clamp. The endoscope clamp holds the endoscope in a fixed position relative to the endoscopic cleaning and lubrication system. The gooseneck tube is a flexible structure that allows for the repositioning of the endoscope clamp.

These together with additional objects, features and advantages of the endoscopic cleaning and lubrication system will be readily apparent to those of ordinary skill in the art upon reading the following detailed description of the presently preferred, but nonetheless illustrative, embodiments when taken in conjunction with the accompanying drawings.

In this respect, before explaining the current embodiments of the endoscopic cleaning and lubrication system in detail, it is to be understood that the endoscopic cleaning and lubrication system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the endoscopic cleaning and lubrication system.

It is therefore important that the claims be regarded as including such equivalent construction insofar as they do not depart from the spirit and scope of the endoscopic cleaning and lubrication system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 8 is a detail view of an embodiment of the disclosure.

FIG. 9 is a detail view of an embodiment of the disclosure.

FIG. 10 is a detail view of an embodiment of the disclosure.

FIG. 11 is a detail view of an embodiment of the disclosure.

FIG. 12 is a detail view of an embodiment of the disclosure.

FIG. 13 is a detail view of an embodiment of the disclosure.

FIG. 14 is a detail view of an embodiment of the disclosure.

FIG. 15 is a detail view of an embodiment of the disclosure.

FIG. 16 is a detail view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
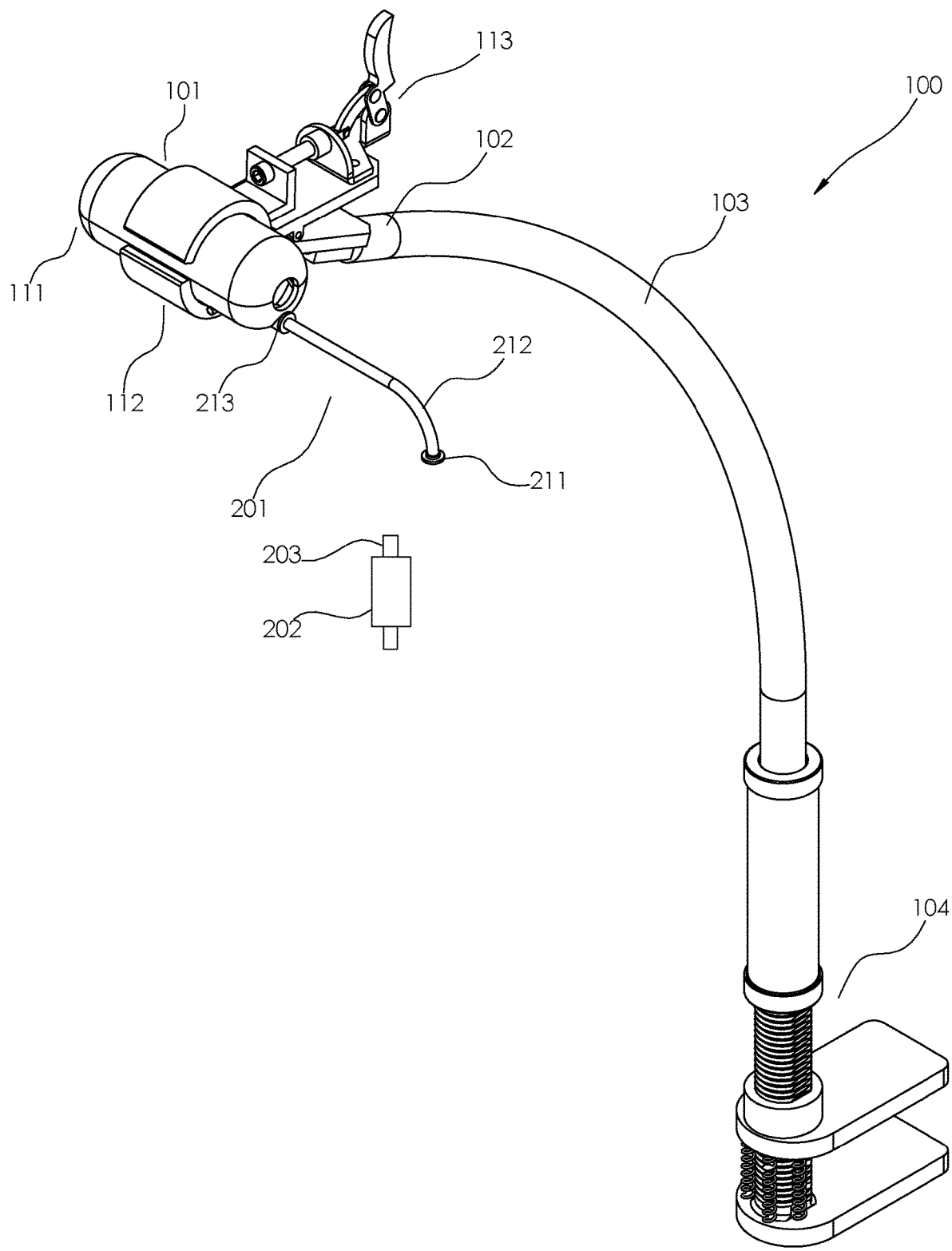
FIG. 1 is a perspective view of an embodiment of the disclosure.
Figure 2:
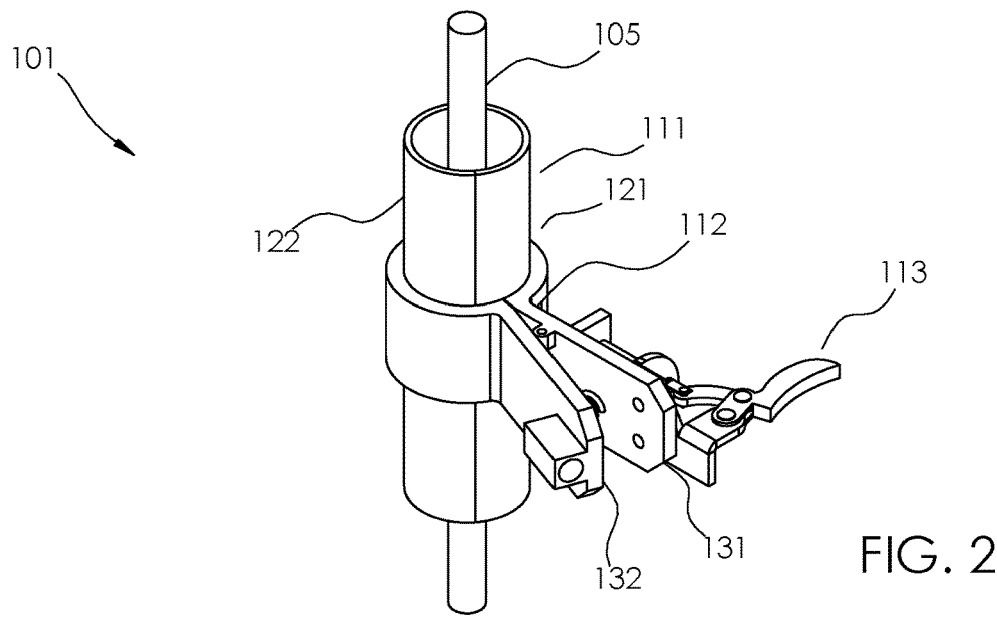
FIG. 2 is a detail view of an embodiment of the disclosure.
Figure 3:
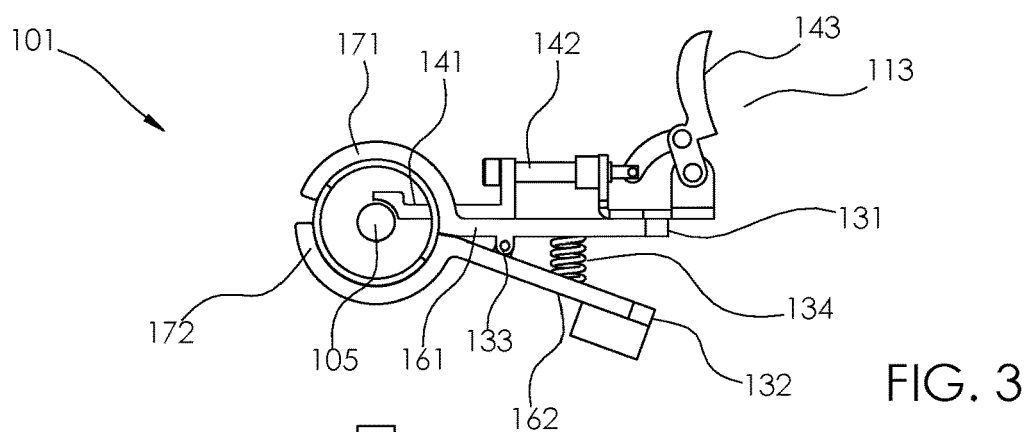
FIG. 3 is a detail view of an embodiment of the disclosure.
Figure 4:
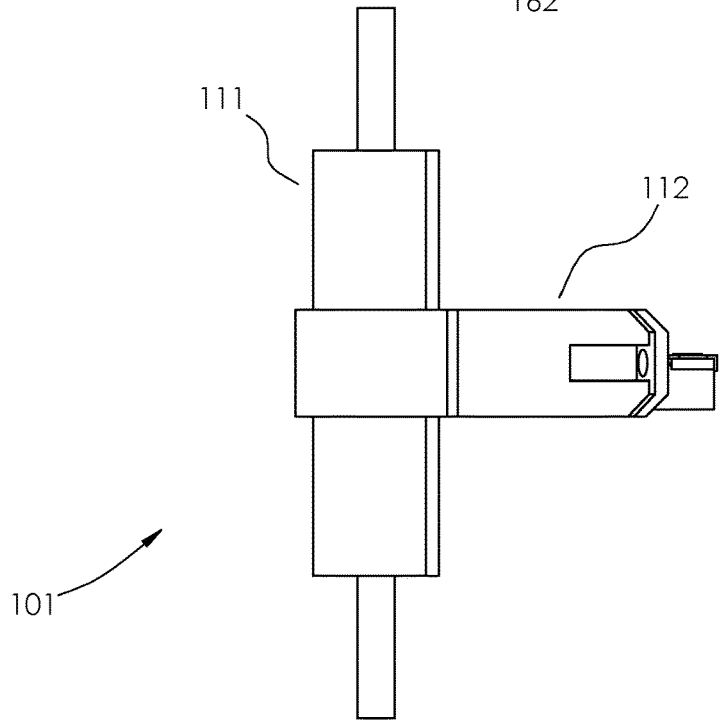
FIG. 4 is a detail view of an embodiment of the disclosure.
Figure 5:
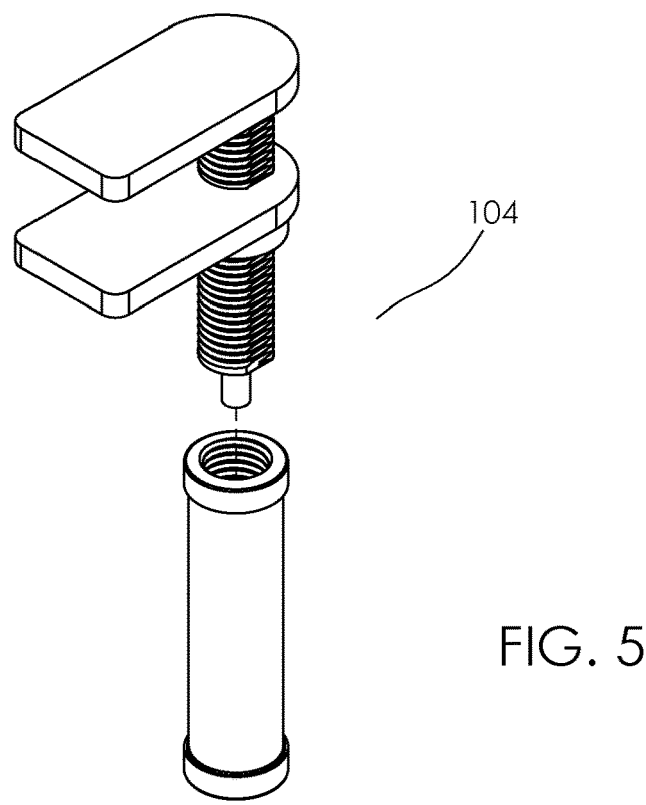
FIG. 5 is a detail view of an embodiment of the disclosure.
Figure 6:
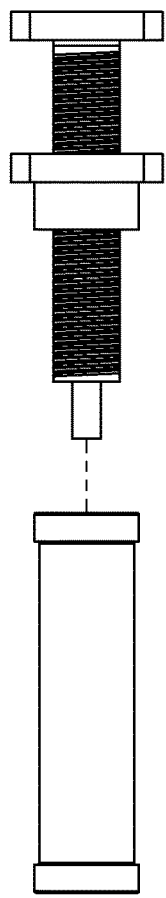
FIG. 6 is a detail view of an embodiment of the disclosure.
Figure 7:
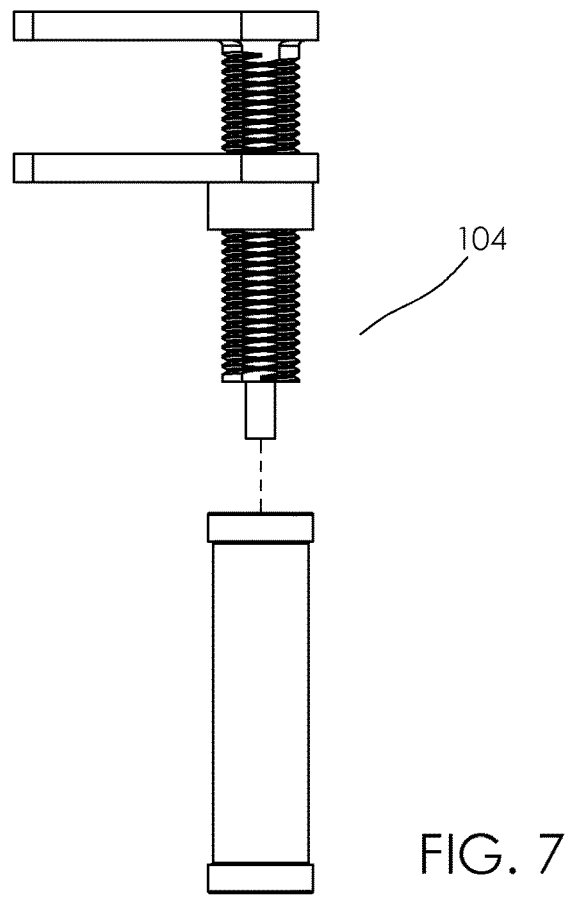
FIG. 7 is a detail view of an embodiment of the disclosure.
Figure 17:
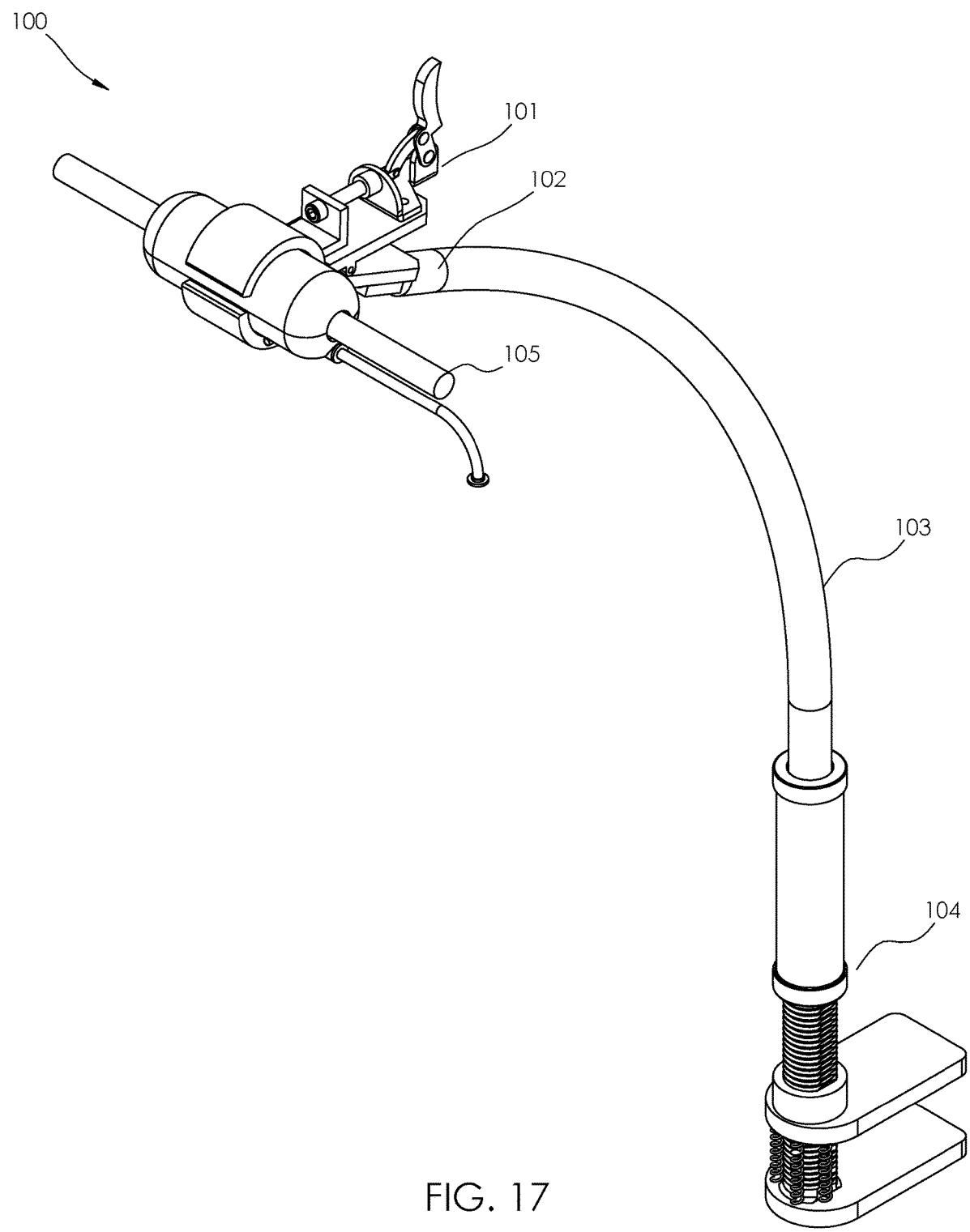
FIG. 17 is an in-use view of an embodiment of the disclosure.

Detailed reference will now be made to one or more potential embodiments of the disclosure, which are illustrated in FIGS. 1 through 17.

The endoscopic cleaning and lubrication system 100 (hereinafter invention) is a mechanical structure. The invention 100 is a medical device. The invention 100 is configured for use with an endoscope 105. The invention 100 clamps the endoscope 105 to a working surface, such as an operating table, such that the endoscope 105 can be cleaned and lubricated before use in a medical procedure. The invention 100 comprises an endoscope 105 clamp 101, a clamp mount 102, a gooseneck tube 103, and a table clamp 104. The gooseneck tube 103 attaches the clamp mount 102 to the table clamp 104. The table clamp 104 attaches the invention 100 to the working surface. The clamp mount 102 attaches the endoscope 105 clamp 101 to the gooseneck tube 103. The endoscope 105 attaches to the endoscope 105 clamp 101. The endoscope 105 clamp 101 holds the endoscope 105 in a fixed position relative to the invention 100. The gooseneck tube 103 is a flexible structure that allows for the repositioning of the endoscope 105 clamp 101.

The endoscope 105 is a prism-shaped structure. The endoscope 105 is defined elsewhere in this disclosure. The gooseneck tube 103 is defined elsewhere in this disclosure.

The clamp mount 102 is a fastening structure. The clamp mount 102 attaches the endoscope 105 clamp 101 to the gooseneck tube 103 such that a fixed position is maintained between the endoscope 105 clamp 101 and the gooseneck tube 103. The gooseneck tube 103 is a flexible structure that elevates the endoscope 105 clamp 101 above a working surface.

The table clamp 104 is a fastening structure. The table clamp 104 attaches to the end of the gooseneck tube 103 that is distal from the endoscope 105 clamp 101. The table clamp 104 removably attaches the gooseneck tube 103 to the working surface.

The endoscope 105 clamp 101 is a clip. The endoscope 105 clamp 101 is a spring-loaded structure. The endoscope 105 clamp 101 grasps the exterior lateral faces of the prism structure of the endoscope 105. The endoscope 105 clamp 101 holds the endoscope 105 in a fixed position relative to the clamp mount 102. The endoscope 105 clamp 101 comprises a clamp vessel 111, a vessel grip 112, and a retaining structure 113.

The clamp vessel 111 is a mechanical structure. The clamp vessel 111 is a hollow ovoid structure. The clamp vessel 111 encloses the lateral face of the prism structure of the endoscope 105 such that the endoscope 105 removably attaches to the endoscope 105 clamp 101. The endoscope 105 inserts through the clamp vessel 111 such that the endoscope 105 slides through the clamp vessel 111 while attached to the endoscope 105 clamp 101. The clamp vessel 111 comprises a superior shell 121, an inferior shell 122, a first aperture 151, and a second aperture 152.

The superior shell 121 is a non-Euclidean disk-shaped structure. The superior shell 121 forms one half of the ovoid structure of the clamp vessel 111. The superior shell 121 is bifurcated from the inferior shell 122 such that the major axis of the ovoid that forms the clamp vessel 111 is contained within the plane that bifurcates the clamp vessel 111. The superior shell 121 forms the superior surfaces of the clamp vessel 111.

The inferior shell 122 is a non-Euclidean disk-shaped structure. The inferior shell 122 forms one half of the ovoid structure of the clamp vessel 111. The inferior shell 122 is bifurcated from the superior shell 121 such that the major axis of the ovoid that forms the clamp vessel 111 is contained within the plane that bifurcates the clamp vessel 111. The inferior shell 122 forms the inferior surfaces of the clamp vessel 111. The inferior shell 122 is identical to the superior shell 121.

The first aperture 151 is a negative space that is formed through the exterior surface of the clamp vessel 111. The first aperture 151 has a non-Euclidean disk structure. The center of the non-Euclidean disk structure of the first aperture 151 aligns with the major axis of the ovoid structure of the clamp vessel 111. The first aperture 151 is further formed with a first taper 221 that prevents the endoscope 105 from getting stuck within the clamp vessel 111. Specifically, the first taper 221 is a configuration of the concave interior surface of the clamp vessel 111. The first taper 221 forms a concave structure that funnels the endoscope 105 towards the first aperture 151 as the endoscope passes through the clamp vessel 111. The first taper 221 prevents the endoscope 105 from getting caught within in the clamp vessel 111 during a procedure.

The second aperture 152 is a negative space that is formed through the exterior surface of the clamp vessel 111. The second aperture 152 has a non-Euclidean disk structure. The center of the non-Euclidean disk structure of the second aperture 152 aligns with the major axis of the ovoid structure of the clamp vessel 111. The position of the second aperture 152 on the clamp vessel 111 is at the point of the clamp vessel 111 that is distal from the first aperture 151. The second aperture 152 is further formed with a second taper 222 that prevents the endoscope 105 from getting stuck within the clamp vessel 111. Specifically, the second taper 222 is a configuration of the concave interior surface of the clamp vessel 111. The second taper 222 forms a concave structure that funnels the endoscope 105 towards the second aperture 152 as the endoscope passes through the clamp vessel 111. The second taper 222 prevents the endoscope 105 from getting caught within the clamp vessel 111 during a procedure.

The vessel grip 112 is a mechanical structure. The vessel grip 112 is a fastening structure. The vessel grip 112 attaches the clamp vessel 111 to the clamp mount 102 such that a fixed position is maintained between the clamp vessel 111 and the clamp mount 102. The vessel grip 112 comprises a superior plate 131, an inferior plate 132, a hinge 133, and a compression spring 134.

The superior plate 131 is a non-Euclidean disk-shaped structure. The superior plate 131 forms a concave surface that fits flush against the convex surface of the superior shell 121. The superior plate 131 forms a portion of the grasping structure of the endoscope 105 clamp 101. The retaining structure 113 attaches to the superior plate 131. The superior plate 131 comprises a superior flat disk 161 and a superior non-Euclidean disk 162.

The superior flat disk 161 is a disk-shaped structure. The superior flat disk 161 has a rectangular shape. The retaining structure 113 attaches to the superior face of the superior flat disk 161. The superior non-Euclidean disk 162 is a prism structure. The superior non-Euclidean disk 162 has a non-Euclidean disk-shaped structure. The congruent ends of the superior non-Euclidean disk 162 are formed with a curvature that is geometrically similar to the superior shell 121 of the clamp vessel 111 such that the convex surface of the superior shell 121 fits flush against the concave surface formed by the superior non-Euclidean disk 162. The lateral face of the superior non-Euclidean disk 162 attaches to the lateral face of the superior flat disk 161 such that the superior flat disk 161 and the superior non-Euclidean disk 162 combine to form the single unified structure of the superior plate 131.

The inferior plate 132 is a non-Euclidean disk-shaped structure. The inferior plate 132 forms a concave surface that fits flush against the convex surface of the inferior shell 122. The inferior plate 132 forms a portion of the grasping structure of the endoscope 105 clamp 101. The inferior plate 132 attaches to the clamp mount 102. The inferior plate 132 comprises an inferior flat disk 171 and an inferior non-Euclidean disk 172.

The inferior flat disk 171 is a disk-shaped structure. The inferior flat disk 171 has a rectangular shape. The retaining structure 113 attaches to the superior face of the inferior flat disk 171. The inferior non-Euclidean disk 172 is a prism structure. The inferior non-Euclidean disk 172 has a non-Euclidean disk-shaped structure. The congruent ends of the inferior non-Euclidean disk 172 are formed with a curvature that is geometrically similar to the superior shell 121 of the clamp vessel 111 such that the convex surface of the superior shell 121 fits flush against the concave surface formed by the inferior non-Euclidean disk 172. The lateral face of the inferior non-Euclidean disk 172 attaches to the lateral face of the inferior flat disk 171 such that the inferior flat disk 171 and the inferior non-Euclidean disk 172 combine to form the single unified structure of the inferior plate 132.

The retaining structure 113 is a mechanical structure. The retaining structure 113 is an adjustable structure. The retaining structure 113 secures the endoscope 105 within the clamp vessel 111 such that the range of motion of the endoscope 105 in a direction perpendicular to the prism structure of the endoscope 105 is limited. The retaining structure 113 comprises a retaining cantilever 141, a worm drive 142, and a locking mechanism 143. The clamp vessel 111 and the retaining structure 113 attach to the vessel grip 112.

The retaining cantilever 141 is a mechanical structure that attaches to the worm drive 142 in the manner of a cantilever. The free end of the retaining cantilever 141 inserts through the convex surface of the lateral face of the superior non-Euclidean disk 162 of the superior plate 131 and the convex surface of the lateral face of the superior shell 121 of the clamp vessel 111 such that the free end of the retaining cantilever 141 inserts into the hollow interior of the superior shell 121 of the clamp vessel 111. The retaining cantilever 141 rests on the superior surface of the lateral face of the prism structure of the endoscope 105.

The worm drive 142 is a mechanical structure. The worm drive 142 is a rotating structure that adjusts the position of the free end of the retaining cantilever 141 within the hollow interior of the superior shell 121 of the clamp vessel 111. The worm drive 142 is defined elsewhere in this disclosure.

The locking mechanism 143 is a mechanical structure. The locking mechanism 143 locks the worm drive 142 in a fixed position such that the position of the free end of the retaining cantilever 141 is locked into a fixed position within the superior shell 121 of the clamp vessel 111.

The hinge 133 is a rotating fastening device. The hinge 133 attaches the superior plate 131 to the inferior plate 132 such that the superior plate 131 rotates relative to the inferior plate 132. The compression spring 134 is a spring that stores mechanical energy when compressed and releases the stored mechanical energy when the compression spring 134 returns to its relaxed shape.

The compression spring 134 attaches the superior plate 131 to the inferior plate 132. The compression spring 134 presses the concave surfaces of the superior plate 131 and the inferior plate 132 against the convex surfaces of the superior shell 121 and the inferior shell 122. The compression spring 134 provides the motive forces that secures the clamp vessel 111 to the vessel grip 112.

In a second potential embodiment of the disclosure, the clamp vessel 111 further comprises a lubricant port 201. The lubricant port 201 is configured for use with a Luer syringe 202. The Luer syringe 202 further comprises a Luer taper.

The lubricant port 201 forms a fluidic connection between the Luer syringe 202 and the interior of the clamp vessel 111. The lubricant port 201: a) transports a lubricant injected into lubricant port 201 by the Luer syringe 202 into the interior space of the clamp vessel 111; and, b) diffuses the lubricant within the clamp vessel 111 such that lubricant is applied evenly to the endoscope 105.

The lubricant port 201 comprises a Luer slip 211, a lubricant hose 212, a transfer port 213, and a diffusion sponge 214. The Luer slip 211 and the transfer port 213 attach to the lubricant hose 212. The diffusion sponge 214 is fluidically connected to the transfer port 213.

The Luer slip 211 receives the lubricant injected into lubricant port 201 by the Luer syringe 202. The Luer slip 211 is sized to receive the Luer taper 203 of the Luer syringe 202 during the transfer process. The lubricant hose 212 forms a fluidic connection between the Luer slip 211 and the transfer port 213. The transfer port 213 receives the lubricant from the lubricant hose 212 and transfers the received lubricant to the diffusion sponge 214.

The diffusion sponge 214 attaches to the clamp vessel 111 such that: a) the diffusion sponge 214 covers the interior concave surfaces of the clamp vessel 111; and, b) the diffusion sponge 214 is in contact with the endoscope 105 as the endoscope passes through the clamp vessel 111.

The diffusion sponge 214 receives the lubricant from the transfer port 213. The diffusion sponge 214 diffuses the lubricant evenly throughout the structure of the diffusion sponge 214 using capillary action. The contact of the diffusion sponge 214 with the endoscope 105 allows the diffusion sponge 214 to apply an evenly distributed layer to the lateral face of the prism-like structure of the endoscope 105.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Catheter: As used in this disclosure, a catheter is a flexible tube that is inserted into the body through which images may be captured and fluids may be introduced into or removed from the body. Endoscope is a synonym for catheter.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid.

When the center axes of two cylinder, prism or pyramidal structures share the same line they are said to be aligned. When the center axes of two cylinder, prism or pyramidal structures do not share the same line they are said to be offset.

Clip: As used in this disclosure, a clip is a fastener that attaches to an object by gripping or clasping the object. A clip is typically spring loaded.

Compression Spring: As used in this disclosure, a compression spring is a spring that resists forces attempting to compress the spring in the direction of the center axis of the spring. The compression spring will return to its original position when the compressive force is removed.

Concave: As used in this disclosure, concave is used to describe: 1) a surface that resembles the interior surface of a sphere; or, 2) a function with a curvature structure wherein a chord that connects any two points of the function will be lesser than (graphically below) or equal to the value of the function at any point along the chord.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Convex: As used in this disclosure, convex is used to describe: 1) a surface that resembles the outer surface of a sphere; or, 2) a function with a curvature structure wherein a chord that connects any two points of the function will be greater than (graphically above) or equal to the value of the function at any point along the chord.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Exterior Screw Thread: An exterior screw thread is a ridge wrapped around the outer surface of a tube in the form of a helical structure that is used to convert rotational movement into linear movement.

Flexible: As used in this disclosure, flexible refers to an object or material that will deform when a force is applied to it but that will not necessarily return to its original shape when the deforming force is removed.

Flush: As used in this disclosure, the term flush is used to describe the alignment of a first surface and a second surface to form a single structure selected from the group consisting of a Euclidean plane and a non-Euclidean plane.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Gooseneck Tube or Gooseneck Mount: As used in this disclosure, a gooseneck tube is a flexible tubular semi-rigid structure. The semi-rigid structure of the gooseneck tube has an inelastic nature such that the gooseneck tube holds its new shape after the gooseneck tube has been deformed. The gooseneck tube is commonly used as a mounting device for domestic articles. Specifically, the gooseneck tube: 1) attaches the domestic article to a stationary object; in such a manner that, 2) the position of the domestic article relative to the user is adjusted by bending the gooseneck tube. The typical gooseneck tube comprises a first coiled wire wrapped around a second reinforcing wire. The first coiled wire allows a gooseneck tube to be bent into the desired position. The second reinforcing wire enhances the strength and stability of the gooseneck tube while the gooseneck tube is supporting a load.

Hinge: As used in this disclosure, a hinge is a device that permits the turning, rotating, or pivoting of a first object relative to a second object. A hinge designed to be fixed into a set position after rotation is called a locking hinge.

Inferior: As used in this disclosure, the term inferior refers to a directional reference that is parallel to and in the same direction as the force of gravity when an object is positioned or used normally.

Interior Screw Thread: An interior screw thread is a groove that is formed around the inner surface of a tube in the form of a helical structure that is used to convert rotational movement into linear movement.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Lock: As used in this disclosure, a lock is a fastening device that secures a rotating mechanical device into a fixed position.

Major and Minor Axes: As used in this disclosure, the major and minor axes refer to a pair of perpendicular axes that are defined within a structure. The length of the major axis is always greater than or equal to the length of the minor axis. The major axis forms the longest symmetric bifurcation of the structure. The major and minor axes intersect at the center of the structure. The major axis is always parallel or perpendicular to an edge of a rectangular or rectilinear structure.

Mount: As used in this disclosure, a mount is a mechanical structure that attaches or incorporates a first object to a second object.

Non-Euclidean Prism: As used in this disclosure, a non-Euclidean prism is a prism structure wherein the center axis of the prism lies on a non-Euclidean plane or is otherwise formed with a curvature.

Non-Euclidean Structure: As used in this disclosure, a non-Euclidean structure is a structure wherein an axis of the structure lies on a non-Euclidean plane or is otherwise formed with a curvature.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Oval: As used in this disclosure, an oval is a geometric shape that is formed in the shape of a "squished" circle similar in form to an ellipse. The difference between an oval and an ellipse is that an ellipse can be described by a mathematical formula while an oval has no such formal description. The term ovoid refers to a three-dimensional structure with an oval shape that is analogous to the relationship of an ellipsoid and an ellipse.

Perimeter: As used in this disclosure, a perimeter is one or more curved or straight lines that bounds an enclosed area on a plane or surface. The perimeter of a circle is commonly referred to as a circumference.

Pivot: As used in this disclosure, a pivot is a rod or shaft around which an object rotates or swings.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Superior: As used in this disclosure, the term superior refers to a directional reference that is parallel to and in the opposite direction of the force of gravity when an object is positioned or used normally.

Threaded Connection: As used in this disclosure, a threaded connection is a type of fastener that is used to join a first cylindrical object and a second cylindrical object together. The first cylindrical object is fitted with a first fitting selected from an interior screw thread or an exterior screw thread. The second cylindrical object is fitted with the remaining screw thread. The cylindrical object fitted with the exterior screw thread is placed into the remaining cylindrical object such that: 1) the interior screw thread and the exterior screw thread interconnect; and, 2) when the cylindrical object fitted with the exterior screw thread is rotated the rotational motion is converted into linear motion that moves the cylindrical object fitted with the exterior screw thread either into or out of the remaining cylindrical object. The direction of linear motion is determined by the direction of rotation.

Worm Drive: As used in this disclosure, a worm drive refers to a mechanical arrangement where a rotating cylinder further comprising an exterior screw thread is used to: 1) rotate a gear; or 2) move a plate formed with an interior screw thread in a linear fashion in the direction of the center axis of the rotating cylinder. Worm drives are also referred to as worm gears.

With respect to the above description, it is to be realized that the optimum dimensional relationship for the various components of the invention described above and in FIGS. 1 through 17 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An endoscopic cleaning and lubrication system comprising
    an endoscope clamp, a clamp mount, a gooseneck tube, and a table clamp;
    wherein the gooseneck tube attaches the clamp mount to the table clamp;
    wherein the table clamp is configured to attach to a working surface;
    wherein the clamp mount attaches the endoscope clamp to the gooseneck tube;
    wherein the endoscopic cleaning and lubrication system is a medical device;
    wherein the endoscopic cleaning and lubrication system is a mechanical structure;
    wherein the endoscopic cleaning and lubrication system configured for use with an endoscope;
    wherein the endoscopic cleaning and lubrication system is configured to support and enable the endoscope to pass forward and rearward when in use;
    wherein the endoscope clamp comprises a clamp vessel, a vessel grip, and a retaining structure;
    wherein the clamp vessel further comprises a lubricant port;
    wherein the lubricant port is configured for use with a Luer syringe;
    wherein the Luer syringe further comprises a Luer taper;
    wherein the lubricant port forms a fluidic connection between the Luer syringe and an interior of the clamp vessel;

wherein the lubricant port transports a fluid injected into lubricant port by the Luer syringe into the interior of the clamp vessel;

wherein the lubricant port diffuses the fluid within the clamp vessel.

2. The endoscopic cleaning and lubrication system according to claim 1 wherein the endoscope attaches to the endoscope clamp;

wherein the endoscope clamp is configured to hold the endoscope in a fixed position relative to the working surface;

wherein the gooseneck tube is a flexible structure that allows for the repositioning of the endoscope clamp.

3. The endoscopic cleaning and lubrication system according to claim 2 wherein the clamp mount is a fastening structure;

wherein the clamp mount attaches the endoscope clamp to the gooseneck tube such that a fixed position is maintained between the endoscope clamp and the gooseneck tube.

4. The endoscopic cleaning and lubrication system according to claim 3 wherein the gooseneck tube is a flexible structure that supports the endoscope clamp at a position relative the table clamp;

wherein the table clamp is a fastening structure;

wherein the table clamp attaches to the end of the gooseneck tube that is distal from the endoscope clamp.

5. The endoscopic cleaning and lubrication system according to claim 4 wherein the endoscope clamp is a clip;

wherein the endoscope clamp is a spring-loaded structure;

wherein the endoscope clamp is configured to support exterior lateral faces of the endoscope;

wherein the endoscope clamp is configured to enable the endoscope to slide back and forth when in use.

6. The endoscopic cleaning and lubrication system according to claim 5 wherein the vessel grip attaches the clamp vessel to the clamp mount such that a fixed position is maintained between the clamp vessel and the clamp mount;

wherein the retaining structure attaches to the vessel grip.

7. The endoscopic cleaning and lubrication system according to claim 6 wherein the clamp vessel is a mechanical structure;

wherein the clamp vessel is a hollow ovoid structure;

wherein the endoscope is configured to insert through the clamp vessel such that the endoscope slides through the clamp vessel while attached to the endoscope clamp;

wherein a fluid is dispersed within the clamp vessel that is configured for either cleaning or lubricating the endoscope.

8. The endoscopic cleaning and lubrication system according to claim 7 wherein the clamp vessel comprises a superior shell, an inferior shell, a first aperture, and a second aperture;

wherein the superior shell is a non-Euclidean disk-shaped structure;

wherein the superior shell forms one half of the ovoid structure of the clamp vessel;

wherein the inferior shell is a non-Euclidean disk-shaped structure;

wherein the inferior shell forms one half of the ovoid structure of the clamp vessel;

wherein the first aperture is a negative space that is formed through the exterior surface of the clamp vessel;

wherein the second aperture is a negative space that is formed through the exterior surface of the clamp vessel;

wherein the superior shell is bifurcated from the inferior shell such that the major axis of the ovoid that forms the clamp vessel is contained within the plane that bifurcates the clamp vessel.

9. The endoscopic cleaning and lubrication system according to claim 8 wherein the superior shell forms the superior surfaces of the clamp vessel;

wherein the inferior shell forms the inferior surfaces of the clamp vessel.

10. The endoscopic cleaning and lubrication system according to claim 9 wherein the first aperture has a non-Euclidean disk structure;

wherein the center of the non-Euclidean disk structure of the first aperture aligns with the major axis of the ovoid structure of the clamp vessel;

wherein the second aperture has a non-Euclidean disk structure;

wherein the center of the non-Euclidean disk structure of the second aperture aligns with the major axis of the ovoid structure of the clamp vessel;

wherein the position of the second aperture on the clamp vessel is at the point of the clamp vessel that is distal from the first aperture.

11. The endoscopic cleaning and lubrication system according to claim 10 wherein the vessel grip comprises a superior plate, an inferior plate, a hinge, and a compression spring;

wherein the superior plate is a non-Euclidean disk-shaped structure;

wherein the inferior plate is a non-Euclidean disk-shaped structure.

12. The endoscopic cleaning and lubrication system according to claim 11 wherein the superior plate forms a concave surface that fits flush against the convex surface of the superior shell;

wherein the inferior plate forms a concave surface that fits flush against the convex surface of the inferior shell;

wherein the retaining structure attaches to the superior plate;

wherein the inferior plate attaches to the clamp mount.

13. The endoscopic cleaning and lubrication system according to claim 12 wherein the superior plate comprises a superior flat disk and a superior non-Euclidean disk;

wherein the superior non-Euclidean disk attaches to the the superior flat disk.

14. The endoscopic cleaning and lubrication system according to claim 13 wherein the retaining structure attaches to a superior face of the superior flat disk;

wherein congruent ends of the superior non-Euclidean disk are formed with a curvature that is geometrically similar to the superior shell of the clamp vessel such that the convex surface of the superior shell fits flush against the concave surface formed by the superior non-Euclidean disk;

wherein a lateral face of the superior non-Euclidean disk attaches to the lateral face of the superior flat disk such that the superior flat disk and the superior non-Euclidean disk combine to form the single unified structure of the superior plate.

15. The endoscopic cleaning and lubrication system according to claim 14
- wherein the inferior plate comprises an inferior flat disk and an inferior non-Euclidean disk;
- wherein the inferior non-Euclidean disk attaches to the inferior flat disk.

16. The endoscopic cleaning and lubrication system according to claim 15
- wherein the retaining structure attaches to the superior face of the inferior flat disk;
- wherein the congruent ends of the inferior non-Euclidean disk are formed with a curvature that is geometrically similar to the superior shell of the clamp vessel such that the convex surface of the superior shell fits flush against the concave surface formed by the inferior non-Euclidean disk;
- wherein the lateral face of the inferior non-Euclidean disk attaches to the lateral face of the inferior flat disk such that the inferior flat disk and the inferior non-Euclidean disk combine to form the single unified structure of the inferior plate.

17. The endoscopic cleaning and lubrication system according to claim 16
- wherein the retaining structure is a mechanical structure;
- wherein the retaining structure is an adjustable structure;
- wherein the retaining structure is configured to secure the endoscope within the clamp vessel such that the range of motion of the endoscope is limited.

18. The endoscopic cleaning and lubrication system according to claim 17
- wherein the retaining structure comprises a retaining cantilever, a worm drive, and a locking mechanism;
- wherein the clamp vessel and the retaining structure attach to the vessel grip;
- wherein the retaining cantilever is a mechanical structure that attaches to the worm drive in the manner of a cantilever;
- wherein a free end of the retaining cantilever inserts through the convex surface of the lateral face of the superior non-Euclidean disk of the superior plate and the convex surface of the lateral face of the superior shell of the clamp vessel such that the free end of the retaining cantilever inserts into the hollow interior of the superior shell of the clamp vessel;
- wherein the worm drive is a mechanical structure;
- wherein the worm drive is a rotating structure that adjusts the position of the free end of the retaining cantilever within the hollow interior of the superior shell of the clamp vessel;
- wherein the locking mechanism is a mechanical structure;
- wherein the locking mechanism locks the worm drive in a fixed position such that the position of the free end of the retaining cantilever is locked into a fixed position within the superior shell of the clamp vessel;
- wherein the hinge is a rotating fastening device;
- wherein the hinge attaches the superior plate to the inferior plate such that the superior plate rotates relative to the inferior plate;
- wherein the compression spring attaches the superior plate to the inferior plate;
- wherein the compression spring presses the concave surfaces of the superior plate and the inferior plate against the convex surfaces of the superior shell and the inferior shell.

19. The endoscopic cleaning and lubrication system according to claim 18
- wherein the fluid is either a lubricant that is configured to lubricate the endoscope or a cleaning agent that is configured to remove gross contaminants from the endoscope;
- wherein the lubricant port comprises a Luer slip, a lubricant hose, a transfer port, and a diffusion sponge;
- wherein the Luer slip and the transfer port attach to the lubricant hose;
- wherein the diffusion sponge is fluidically connected to the transfer port;
- wherein the Luer slip receives the lubricant injected into lubricant port by the Luer syringe;
- wherein the Luer slip is sized to receive the Luer taper of the Luer syringe during a transfer process;
- wherein the lubricant hose forms a fluidic connection between the Luer slip and the transfer port;
- wherein the transfer port receives the fluid from the lubricant hose and transfers the received fluid to the diffusion sponge;
- wherein the diffusion sponge attaches to the clamp vessel such that: a) the diffusion sponge covers the interior concave surfaces of the clamp vessel; and, b) the diffusion sponge is in contact with the endoscope as the endoscope passes through the clamp vessel;
- wherein the diffusion sponge receives the fluid from the transfer port;
- wherein the diffusion sponge diffuses the fluid evenly throughout the structure of the diffusion sponge.

* * * * *